United States Patent [19]

Egan, Jr.

[11] 3,943,609
[45] Mar. 16, 1976

[54] ADHESIVE DIAPER FASTENER WITH INTEGRAL ADHESIVE PROTECTING MEANS

[75] Inventor: Francis L. Egan, Jr., Arlington Heights, Ill.

[73] Assignee: Colgate-Palmolive Company, New York, N.Y.

[22] Filed: Feb. 4, 1974

[21] Appl. No.: 439,089

[52] U.S. Cl........... 24/73 VA; 24/DIG. 11; 128/287; 428/40; 428/121; 428/352
[51] Int. Cl.² ................. A41B 13/02; B32B 3/04
[58] Field of Search ............ 161/99, 102, 109, 110, 161/113, 145; 117/122 P; 128/156, 284, 287, 290 R; 428/40–43, 54, 55, 77, 121, 124, 131, 132, 198, 202, 343, 352; 24/DIG. 11, 73 VA

[56] References Cited
UNITED STATES PATENTS

| | | | |
|---|---|---|---|
| 2,651,408 | 9/1953 | Engberg et al. | 161/109 |
| 3,221,738 | 12/1965 | Ekberg et al. | 128/287 |
| 3,411,978 | 11/1968 | Frohbach et al. | 161/113 X |
| 3,575,175 | 4/1971 | McGuire | 128/290 R |
| 3,630,201 | 12/1971 | Endres | 128/287 |
| 3,776,234 | 12/1973 | Hoey | 128/287 |
| 3,848,594 | 11/1974 | Buell | 117/122 P X |
| 3,848,596 | 11/1974 | Pennau | 117/122 P X |

*Primary Examiner*—George F. Lesmes
*Assistant Examiner*—Henry F. Epstein

[57] ABSTRACT

A diaper fastener comprising an elongated strip of tape having an adhesive coated surface and a web adhesively secured to that surface in the longitudinally central portion of the strip, the exposed surface of the web having a limited affinity for the adhesive. The adhesive coated surface in one end portion of the strip is in contact with that exposed web surface. An opening is provided through the web whereby regions of adhesive in the end and center portions of the strip of tape which are aligned with the opening in the web are in contact with each other for releasably securing the end portion.

3 Claims, 2 Drawing Figures

ADHESIVE DIAPER FASTENER WITH INTEGRAL ADHESIVE PROTECTING MEANS

BACKGROUND OF THE INVENTION

This invention relates to disposable diaper fasteners of the type employing an adhesive coated tape.

Of the various structures which have proposed for such fasteners, one comprises an adhesive coated tape with a non-adhesive web disposed in a generally central region of the tape. An end portion of the tape is folded over for contact with that web, the exposed surface of the web having been treated with a release agent. The tape end portion may be easily peeled from the web surface while the web remains affixed to the central region of the strip of tape there thus being no need for a removable (and thus separately disposable) sheet for protecting the adhesive in the tape portion against premature contact with a surface to which it might adhere. Since this construction, however, relies on the reduced degree of bonding between the tape end portion and the release treated surface of the web, premature peeling of the tape end portion from that surface remains a possibility.

SUMMARY OF THE INVENTION

In view of the foregoing, it is a principal object of the present invention to provide a diaper fastener of the general type described above which provides improved protection against premature peeling and yet has a bond which is easily overcome by the person applying the diaper.

To achieve these and other objects, a diaper fastener constructed according to the present invention comprises an elongated strip of tape having an adhesive coated surface and a web adhesively secured to that surface in the longitudinally central portion of the web strip, the exposed surface of the web having a limited affinity for the adhesive. The adhesive coated surface in one end portion of the strip is in contact with the web's exposed surface. The web has an opening through it whereby regions of adhesive in the end and central portions of the strip which are aligned with that opening are in contact for releasably securing the end portion. Preferably, the opening is centrally located in the web and the adhesive is an acrylic base adhesive.

BRIEF DESCRIPTION OF THE DRAWING

Other objects, features, and advantages of the invention will appear from the following description of a particular preferred embodiment taken together with the accompanying drawing in which.

DETAILED DESCRIPTION OF A PARTICULAR PREFERRED EMBODIMENT

Figure 1:
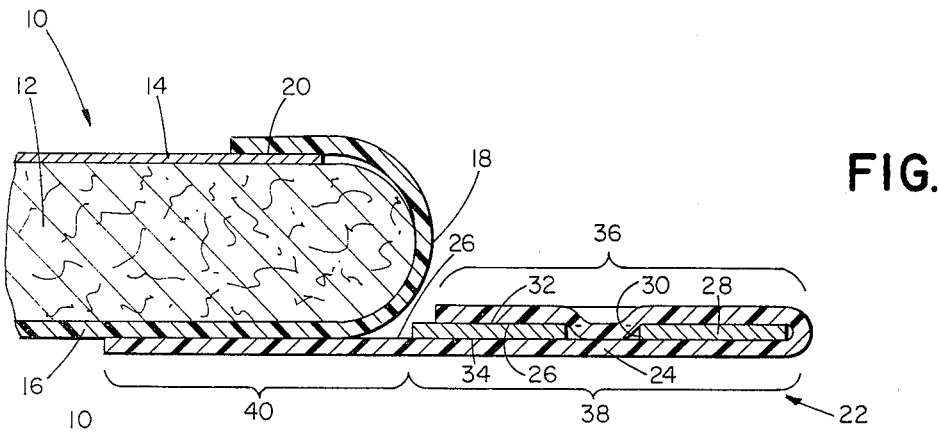
FIG. 1 is a sectional view taken along the diaper fastener longitudinal axis and a portion of the diaper to which it is affixed.

Referring to the drawing, there is shown a lateral portion of a diaper 10 which comprises an absorbent body 12, an inner water pervious liner 14, and an outer water impervious backing 16 which bends around the lateral margin 18 of the diaper and is secured to the liner 14 as at 20.

Figure 2:
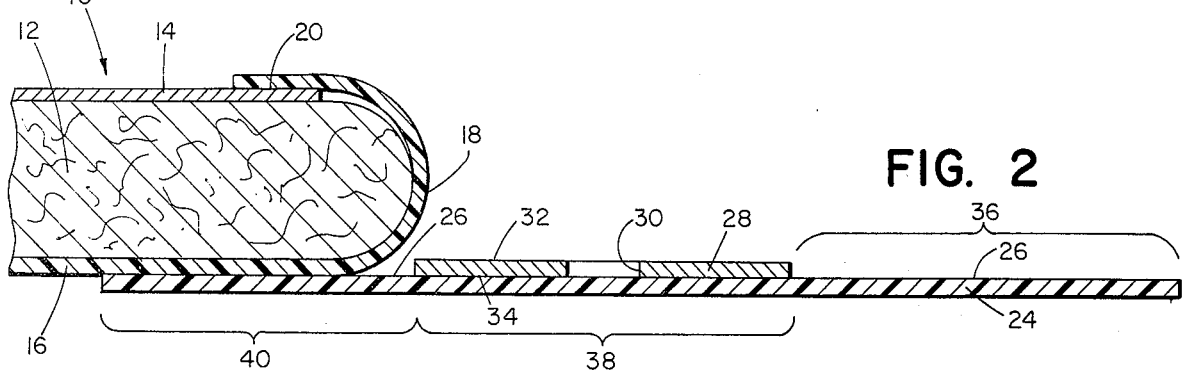
FIG. 2 is a view similar to that of FIG. 1 in which the fastener has been fully extended preparatory to application of the diaper to an infant.

The fastener 22 comprises a strip of tape 24 having an adhesive coated on its surface 26 (see FIG. 2). A web 28 having a centrally located hole 30 therethrough is centrally located on the strip of tape 24 and secured thereto by the adhesive on surface 26. The web 28 may be a craft paper having a release treated upper surface 32 and an untreated lower surface 34. An end portion 36 of the tape 24 is folded over the web 28 (see FIG. 1) to be in contact with the surface 32. In this configuration, the opening 30 produces a contact between portions of the adhesive bearing surface 26 in the tape end portion 36 and tape central portion 38 which are aligned with that opening. The other end portion 40 of the strip of tape 24 has its adhesive coated surface 26 in contact with the backing sheet 16 of the diaper for permanently securing the fastener 22 to the diaper.

In operation, the diaper is presented to the consumer in a configuration shown in FIG. 1. The end portion 36 of the strip of tape 24 may be peeled back from the web 28 by the consumer to achieve the configuration shown in FIG. 2 in which the end portion 36 is available for contact with another portion of the diaper to secure the diaper to an infant. The light tacking of the adhesive on the surface 26 of portion 36 to the release coated surface 32 is reinforced by the adhesive-to-adhesive contact which occurs at the location of the opening 30. The amount of such reinforcement can be adjusted by variations in the size and shape of the opening 30.

In various circumstances, it is preferred that an acrylic base pressure-sensitive adhesive be employed as the coating on surface 26. It has been discovered that such adhesives do not, in general, form as strong an adhesive-to-adhesive bond as do some other pressure-sensitive adhesives commonly employed in tape fasteners for disposable diapers. While acrylic base adhesives do not bond as well to the polyethylene film commonly employed as the diaper backing as do rubber base adhesives, for use with other backing materials the acrylic base adhesives may be distinctly preferable.

While a particular preferred embodiment has been illustrated in the accompanying drawing and described in detail herein, other embodiments are within the scope of the invention and following claims.

I claim:

1. A diaper fastener comprising an elongated strip of tape having an adhesive coated surface and a web adhesively secured to and remaining affixed to said surface in the longitudinally central portion of said strip of tape, the exposed surface of said web having limited affinity for said adhesive, said adhesive coated surface in one end portion of said strip of tape in contact with said web exposed surface, said web having an opening therethrough whereby regions of adhesive in said end and central portions aligned with said opening are in contact for releasably securing said end portion.

2. A diaper fastener as claimed in claim 1 wherein said opening is centrally located in said web.

3. A diaper fastener as claimed in claim 1 wherein said adhesive is an acrylic base adhesive.

* * * * *